United States Patent [19]

Reddy

[11] 4,415,548

[45] Nov. 15, 1983

[54] SPERMICIDALLY LUBRICATED PROPHYLACTICS AND METHOD FOR MAKING SAME

[75] Inventor: K. Prakash Reddy, Anderson, S.C.

[73] Assignee: Schmid Laboratories, Inc., West Little Falls, N.J.

[21] Appl. No.: 373,654

[22] Filed: Apr. 30, 1982

Related U.S. Application Data

[63] Continuation of Ser. No. 120,739, Feb. 12, 1980, abandoned.

[51] Int. Cl.$^3$ .......................... A61F 5/00; A61K 9/70; A61L 31/00; B29C 13/00
[52] U.S. Cl. ........................................ 424/28; 53/428; 53/431; 128/132 R; 206/69; 264/129; 264/301; 264/334; 604/289; 604/349
[58] Field of Search ...................... 424/19, 20, 44, 28; 264/129, 130, 334, 301, 305; 53/428, 431, 469; 128/130, 131, 132, 127; 604/289, 349; 206/69

[56] References Cited

U.S. PATENT DOCUMENTS

| | | | |
|---|---|---|---|
| 2,427,305 | 9/1947 | Sander et al. | 264/301 |
| 2,904,041 | 9/1959 | Brown | 128/132 R |
| 3,136,417 | 6/1964 | Clinch | 128/132 R |
| 3,826,828 | 7/1974 | Morel | 128/132 R |
| 3,876,757 | 4/1975 | Scherm | 128/271 |
| 3,948,262 | 4/1976 | Zaffaroni | 128/272 |
| 4,219,016 | 8/1980 | Drobish et al. | 128/130 |
| 4,322,399 | 3/1982 | Ahmad et al. | 424/DIG. 14 |

FOREIGN PATENT DOCUMENTS 2004462 4/1979 United Kingdom ....... 424/DIG. 14

*Primary Examiner*—Willard E. Hoag
*Attorney, Agent, or Firm*—Darby & Darby

[57] ABSTRACT

A spermicidally active, lubricated prophylactic and method for making same is disclosed. The prophylactic is formed by dip-coating and unrolling the prophylactic and a specific lubricant, polyethylene glycol, and a spermicide are dispensed into the rolled prophylactic, the lubricant causing migration of the spermicide throughout the rolled device.

11 Claims, No Drawings

SPERMICIDALLY LUBRICATED PROPHYLACTICS AND METHOD FOR MAKING SAME

This is a continuation of application Ser. No. 120,739, filed Feb. 12, 1980, now abandoned.

The present invention is directed to a spermicidally lubricated prophylactic product and a method of manufacturing the product which allows substantially the entire length of the inner and outer surfaces of the prophylactic to be coated with a spermicidal agent.

It has been known for some time to provide a rubber contraceptive or prophylactic with a spermicidal compositions. For example, Potts and McDevitt, in *Contraception* Volume 11 No. 6 at pages 701–709 (June 1975) describe the performance of a prophylactic which has been treated with a spermicidal composition comprising 0.4 grams of 4% p-triisopropylphenoxypolyethoxyethanol (Texofor FN 11), 0.025% perfume and 95.975% polyethylene glycol. To insure the maximum efficacy and protection against conception, particularly in the case of an accidental rupture of the contraceptive sheath during or shortly after coitus, it is desirable that the spermicidal composition be present throughout the sheath, which is typically formed of a latex rubber composition or, in some instances from a natural membrane (e.g. sheep cecum). Latex sheaths are normally manufactured by dipping a generally phallic shaped mandrel (ceramic or steel) into a warm latex solution to form a latex film on the mandrel surface, and withdrawing the mandrel after a predetermined immersion time. The most convenient technique for applying the spermicidal composition to the entire sheath would appear to involve immersing the hardened film latex coated mandrel into a second and subsequent bath containing the spermicidal composition prior to unrolling the film from the mandrel. This is undesirable as it requires an additional dipping step. Also the dipping operation is generally unsatisfactory because it is not possible to precisely regulate the quantity of spermicidal agent applied to each sheath and it is difficult to unroll the coated sheaths from the mandrel. Since the sheaths are subsequently sealed in individual foil wrappers, it is also desirable to avoid the presence of an excess quantity of the fluid spermicidal agent, so as to minimize the area that must be wrapped in foil.

It has now been unexpectedly discovered that the contraceptive sheath may be impregnated substantially throughout with a spermicidal lubricant composition in a quick, effective, and reliable manner without applying the spermicidal composition along the entire body of the prophylactic prior to wrapping for use.

Accordingly, it is an object of the present invention to provide a new method for preparing a spermicidally-lubricated prophylactic. It is also an object of the present invention to provide a method of impregnating a prophylactic with a predetermined quantity of a spermicidal agent and a lubricant so that there is reliable protection and elimination of any sperm content during subsequent use. It is a further object of the present invention to provide a method of coating or impregnating a prophylactic sheath with a predetermined quantity of a human spermicidal lubricant.

According to the present invention a method for manufacturing a spermicidally lubricated prophylactic includes the steps of dipping mandrels of predetermined size and shape into a latex bath; withdrawing the mandrels from the latex bath; allowing the latex on said mandrels to harden and dry; rolling up the shaped latex coatings to form a generally flattened ring-shaped cup; placing a predetermined amount of a spermicidal composition onto the exposed portion of the latex sheath within the cup; and sealing the spermicidal containing latex sheath in an airtight container whereby an effective amount of spermicidal composition migrates substantially throughout the latex sheath and coats the interior and exterior walls thereof.

The traditional methods of manufacturing a contraceptive prophylactic involve dipping a phallic shaped ceramic mandrel (which may be stationary or rapidly spinning about its longitudinal axis) of predetermined size into a warm bath containing a natural rubber latex. A circumferential groove is located at the upper end of the mandrel. The mandrel is generally immersed in the latex bath to the top of the groove (i.e. so that the surface of the liquid latex liquid is coincident with the top of the groove). After a predetermined time period the mandrel is withdrawn, covered with a coating of latex. The latex coating conforms to the shape of the mandrel. The coating on the mandrel is allowed to dry, and, traditionally, a lubricant coating material is applied.

The present invention also involves dipping a phallic shaped ceramic or steel mandrel of predetermined size into a warm natural rubber latex bath, withdrawing the mandrel, and allowing the latex coating conforming to the shaped mandrel to harden and dry thereby forming a latex sheath. A thickened ring of latex is formed at the upper end of the prophylactic.

Starting from the upper portion the dry latex sheath is then rolled off the mandrel surface around the thickened latex ring to form a cup-shaped elastic ring of predetermined size and circumference. This results in several layers of latex being rolled around the thickened ring formed at the top (open) end of the sheath with the closed end of the sheath forming a cup within the circumference of the ring. In this form the prophylactic sheath is easily mountable for use during sexual intercourse.

The cup shaped latex sheath is now ready for application of the spermicidal composition. At this point, a measured amount of spermicidal agent is dispensed (e.g. from an overhead burette or needle valve into the latex cup preferably at about the immediate center of the cup within the ring. In a preferred embodiment of the invention the spermicidal agent is dissolved in a lubricant composition (polyethylene glycol-mw 400). In an especially preferred embodiment 0.5 cc of a spermicidal lubricant comprising 5% of a nonylphenoxypolyethoxyethanol and 95% polyethylene glycol mw 400 is dispensed. The contraceptive is then wrapped in an airtight container (e.g. sealed in an aluminum foil packet) and stored for ultimate use by the consumer.

It has been discovered that the spermicidal lubricant deposited in the latex cup will migrate substantially throughout the rolled latex sheath within the airtight package over a period of time (usually between about 1–10 or more days) and effectively cover both sides of the latex with an effective contraceptive amount of spermicidal agent. As such, it is not necessary to coat the latex with spermicidal lubricant while it is on the mandrel or prior to unrolling the sheath. The contraceptive prophylactic may be conveniently packaged and substantially all of the prophylactic will become covered with spermicidal lubricant while contained within the airtight (foil) packaging.

The spermicidal agents that are suitable for use in the process and product of the present invention may be generally classified as liquid nonionic surfactant having an approximately neutral ph. A preferred group of liquid nonionic surfactant compositions for use in the invention are the polyethoxylated nonylphenols having average ethylene oxide contents of 4–12 per mole of nonylphenol including for example tri-isopropylphenoxy polyethoxyethanol, octylphenoxpolyethoxyethanol, and nonyl phenoxypolyethoxyethanol.

A particularly preferred nonionic surfactant is nonylphenoxypolyethoxyethanol, which is marketed under the trade name Hyonic PE-90 by the Diamond Shamrock Corporation, Morristown, N.J. The spermicidal agent is preferably applied to the prophylactic cup admixed with a suitable lubricant composition. Among the lubricant suitable for use in the present invention include pharmaceutically acceptable gels, ointments and creams. Especially preferred as lubricant compositions are polyethylene glycol of molecular weight 300–400. Polyethylene glycol mw 400 is the preferred lubricant composition.

It is important that the spermicidal lubricant composition be formulated to provide an effective contraceptive amount of spermicidal agent. Sheaths in which between about 9 and about 30 mg of nonionic spermicidal agent has been dispersed have been found to provide a consistently effective contraceptive action. While more than 30 mg of the spermicidal agent can be employed to yield satisfactory contraceptive results, it is desirable from the standpoint of safety and cost to use the smallest quantity of spermicidal surfactant that will provide consistent effective contraceptive action. This also avoids the likelihood that an excessive quantity of spermicidal agent will distort or rupture the foil package in which the sheaths are held. Spermicidal lubricant compositions comprising between about 1.8 to about 5.5% by weight of nonionic surfactant and between about 94.5 to about 98.2% by weight of a lubricant composition have been found to provide effective contraceptive and lubricating action. All percents used herein are by weight unless otherwise indicated. The total amount of the spermicide and lubricant composition applied to a prophylactic sheath will generally be between about 0.2 and about 1.0 cubic centimeters (cc); the preferred quantity being about 0.5 cc of a spermicidal lubricant composition comprising about 5% by weight of nonylphenoxypolyethoxyethanol and about 95% by weight of polyethylene glycol 400.

The invention will be better understood with reference to the following non-limiting example which is presented for purposes of illustration.

EXAMPLE I

A group of rolled, talc finished, straight tipped latex condoms were sealed in individual aluminum foil packets. Just prior to sealing 0.3 cc of a spermicidal lubricant comprising 95% by weight polyethylene glycol mw 400 and 5% by weight nonylphenoxypolyethoxyethanol were dispensed through a needle valve into the rolled latex cup (i.e. the area corresponding to the forward tip of the unrolled condom). The foil packages were stored at room temperature. At periodic intervals several foil packs were opened, the spermicidally lubricated condoms removed from the package and completely unrolled on a clean dry straight tipped, stainless steel mandrel. Using a 12 inch steel carpenters square with ⅛th inch gradations, the extent of migration of the spermicidal lubricant composition was measured. Both the minimum and maximum measurements (from the tip) were taken and recorded. The raw and average migration scores (in inches) for days 1, 7, and 14 are reproduced below.

| | DAY NO. 1 | |
|---|---|---|
| SAMPLE # | MINIMUM | MAXIMUM |
| 1 | 4⅛" | 8⅜" |
| 2 | 3⅞" | 8¼" |
| 3 | 3⅛" | 7¾" |
| 4 | 3¾" | 8½" |
| 5 | 3½" | 8¼" |
| 6 | 3¼" | 8¼" |
| 7 | 3⅝" | 8⅜" |
| 8 | 3⅜" | 8⅝" |
| 9 | 3¾" | 8¼" |
| 10 | 3⅞" | 8¼" |
| | 35⅞ avg = 3.58" | 83½ avg = 8.35" |

| | DAY NO. 7 | |
|---|---|---|
| SAMPLE # | MINIMUM | MAXIMUM |
| 1 | 4¾" | 8" |
| 2 | 4⅞" | 8¾" |
| 3 | 5⅛" | 8¾" |
| 4 | 4⅞" | 7" |
| 5 | 4⅞" | 8¼" |
| 6 | 5⅛" | 8⅝" |
| 7 | 5" | 8¾" |
| 8 | 5¾" | 8¼" |
| 9 | 5¼" | 8¾" |
| 10 | 5⅞" | 9" |
| | 51¼ avg = 5.12" | 84¾ avg = 8.47" |

| | DAY NO. 14 | |
|---|---|---|
| SAMPLE # | MINIMUM | MAXIMUM |
| 1 | 5⅜" | 8⅝" |
| 2 | 5¼" | 8¼" |
| 3 | 5⅛" | 8⅝" |
| 4 | 5⅛" | 6¼" |
| 5 | 5⅞" | 8¼" |
| 6 | 5¼" | 7¾" |
| 7 | 5⅛" | 9" |
| 8 | 5¼" | 6¼" |
| 9 | 4⅞" | 8¼" |
| 10 | 6" | 6¾" |
| | 52¾ avg = 5.26" | 78¼ avg = 7.82" |

In all instances, the minimum advance of the spermicidal lubricant along the prophylactic sheath increased with time. This indicates that the spermicidal lubricant is advancing by capillary action along the length of the latex sheath. The maximum penetration figure appears to advance gradually fairly quickly to approximately the full length of the prophylactic, but only a portion of the sheath walls are covered to this extent. Hence, this figure is believed to provide a less meaningful indication of the penetration and existence of an effective contraceptive dose throughout the sheath.

The spermicidal activity of the latex condoms of the invention has been tested and its effectiveness confirmed, both in vivo and vitro.

What is claimed is:

1. A method for manufacturing a lubricated spermicidal male contraceptive which comprises:
   (a) dipping a phallic shaped mandrel of predetermined size into a warm bath consisting of latex rubber;
   (b) withdrawing said mandrel bearing a coating consisting essentially of latex rubber from the latex bath;

(c) allowing the latex rubber coating on said mandrel to harden to form a sheath conforming to the shape of said mandrel;

(d) unrolling the sheath from said mandrel to form a cup;

(e) dispensing an effective contraceptive amount of a migratory pharmaceutical formulation comprising a liquid nonionic surfactant spermicidal agent having an approximately neutral pH, and a polyethylene glycol lubricant composition into the latex cup whereby the pharmaceutical formulation migrates by capillary action substantially throughout the inner and outer surfaces of the latex sheath; and (f) sealing the latex sheath containing said spermicide and said lubricant in an airtight container.

2. The method of claim 1 wherein said effective contraceptive amount comprises from about 0.2 cc to about 1.0 cc of said pharmaceutical formulation.

3. The method of claim 2 which comprises dispensing about 0.5 cc of said pharmaceutical formulation comprising about 5% by weight of said formulation of nonylphenoxypolyethoxyethanol and about 95% by weight of said formulation of polyethylene glycol into said latex cup.

4. A spermicidally lubricated prophylactic produced by the method of claim 3.

5. The method of manufacturing latex sheaths coated substantially throughout with a spermicidal agent which comprises:

forming a blunt-shaped sheath consisting essentially of latex rubber having a closed forward end and a generally circular rearward opening, rolling said sheath up toward the front end along the longitudinal axis of the sheath to form a generally circular cup shaped container having a bowl shaped recess corresponding to the closed forward end of said sheath, dispensing a predetermined quantity of a pharmaceutical formulation into the bowl of said cup, said formulation comprising an effecting contraceptive amount of a nonionic spermicidal agent and a polyethylene glycol lubricant composition, and thereafter sealing said sheath in an airtight enclosure.

6. The method of claim 2 wherein the nonionic surfactant is nonylphenoxypolyethoxyethanol.

7. The method of claim 2 wherein said nonionic surfactant is a polyethoxylated nonylphenol composition having an average ethylene oxide content of from 4-12 moles per mole of nonylphenol.

8. The spermicidally lubricated prophylactic produced by the method of claim 1 or 2.

9. The method of claim 2 wherein the formulation comprises from about 1.8% to about 5.5% by weight of nonionic surfactant and from about 94.5% to about 98.2% by weight of said lubricant composition.

10. The method of claim 9 where the pharmaceutical formulation comprises about 5% by weight of nonylphenoxypolyethoxyethanol and about 95% by weight of polyethylene glycol having a molecular weight of 400.

11. A spermicidally lubricated prophylactic produced by the method of claim 10.

* * * * *